US010537708B2

(12) United States Patent
Vancaillie et al.

(10) Patent No.: US 10,537,708 B2
(45) Date of Patent: Jan. 21, 2020

(54) COCHLEAR IMPLANT ELECTRODE ASSEMBLY INSERTION TOOL

(71) Applicant: Cochlear Limited, Macquarie University (AU)

(72) Inventors: Pierre Vancaillie, Macquarie University (AU); Frank Risi, Newtown (AU)

(73) Assignee: COCHLEAR LIMITED, Macquarie University (AU)

( * ) Notice: Subject to any disclaimer, the term of this patent is extended or adjusted under 35 U.S.C. 154(b) by 263 days.

(21) Appl. No.: 15/655,175

(22) Filed: Jul. 20, 2017

(65) Prior Publication Data

US 2017/0312498 A1    Nov. 2, 2017

Related U.S. Application Data

(63) Continuation of application No. 13/589,083, filed on Aug. 17, 2012, now Pat. No. 9,713,713.

(51) Int. Cl.
*A61M 25/00* (2006.01)
*A61N 1/05* (2006.01)
*A61B 90/11* (2016.01)

(52) U.S. Cl.
CPC ......... *A61M 25/0023* (2013.01); *A61B 90/11* (2016.02); *A61N 1/0541* (2013.01)

(58) Field of Classification Search
CPC . A61M 25/0023; A61M 37/0069; A61N 1/04; A61N 1/05–1/10597; A61B 19/201; A61B 18/1492; A61B 17/3468
See application file for complete search history.

(56) References Cited

U.S. PATENT DOCUMENTS

| | | | | |
|---|---|---|---|---|
| 4,840,622 A | * | 6/1989 | Hardy | A61M 25/0052 604/264 |
| 5,069,673 A | * | 12/1991 | Shwab | A61M 25/0023 604/526 |
| 5,443,493 A | | 8/1995 | Byers et al. | |
| 5,902,282 A | * | 5/1999 | Balbierz | A61M 25/0668 604/158 |
| 6,321,125 B1 | | 11/2001 | Kuzma | |
| 7,063,708 B2 | | 6/2006 | Gibson et al. | |
| 7,949,412 B1 | | 5/2011 | Harrison et al. | |
| 9,713,713 B2 | | 7/2017 | Vancaillie | |
| 2001/0023347 A1 | | 9/2001 | Sharkey et al. | |
| 2001/0027297 A1 | | 10/2001 | Ito | |

(Continued)

OTHER PUBLICATIONS

International Search Report for PCT/IB2013/056718, dated Mar. 6, 2014, 6 pages.

(Continued)

*Primary Examiner* — Wade Miles
(74) *Attorney, Agent, or Firm* — Merchant & Gould P.C.

(57) ABSTRACT

An insertion tool having an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This generally ensures that when the electrode assembly is deployed from the distal end of the insertion guide tube, the electrode assembly and insertion guide tube have a known relative orientation.

18 Claims, 12 Drawing Sheets

(56) References Cited

U.S. PATENT DOCUMENTS

| | | | |
|---|---|---|---|
| 2001/0037136 A1* | 11/2001 | Pianca | A61N 1/056 607/122 |
| 2001/0044624 A1* | 11/2001 | Seraj | A61M 25/0138 606/41 |
| 2002/0032459 A1* | 3/2002 | Horzewski | A61B 17/3439 606/198 |
| 2002/0045862 A1 | 4/2002 | Briscoe et al. | |
| 2002/0143251 A1* | 10/2002 | Richardson | A61M 25/0023 600/434 |
| 2002/0147487 A1* | 10/2002 | Sundquist | A61N 1/056 607/122 |
| 2002/0188252 A1 | 12/2002 | Bardy | |
| 2003/0055377 A1 | 3/2003 | Sirhan et al. | |
| 2004/0220651 A1 | 11/2004 | Kuzma et al. | |
| 2006/0276749 A1 | 12/2006 | Selmon et al. | |
| 2007/0208302 A1* | 9/2007 | Webster | A61M 25/0041 604/103.04 |
| 2007/0265582 A1* | 11/2007 | Kaplan | A61B 17/3468 604/260 |
| 2009/0264862 A1* | 10/2009 | Neidert | A61M 25/0021 604/523 |
| 2010/0030162 A1* | 2/2010 | Cremascoli | A61M 25/0021 604/246 |
| 2011/0201887 A1* | 8/2011 | Greenblatt | A61B 17/3421 600/130 |
| 2011/0257459 A1* | 10/2011 | Sutton | A61M 37/0069 600/7 |
| 2011/0319974 A1 | 12/2011 | Thenuwara et al. | |
| 2012/0016344 A1* | 1/2012 | Kusakabe | A61M 25/0021 604/528 |
| 2012/0083727 A1* | 4/2012 | Barnett | A61F 9/0017 604/22 |
| 2013/0245554 A1* | 9/2013 | Inoue | A61F 9/0017 604/151 |

OTHER PUBLICATIONS

Schurzig et al., "Design of a tool Integrating Force Sensing With Automated Insertion in Cochlear Implantation", IEEE/ASME Transactions on Mechatronics, Apr. 2012, vol. 17, No. 2, pp. 381-389.

* cited by examiner

COCHLEAR IMPLANT ELECTRODE ASSEMBLY INSERTION TOOL

CROSS-REFERENCE TO RELATED APPLICATIONS

This application is a continuation of U.S. patent application Ser. No. 13/589,083, filed Aug. 17, 2012, entitled, "COCHLEAR IMPLANT ELECTRODE ASSEMBLY INSERTION TOOL" now U.S. Pat. No. 9,713,713. The disclosure of this priority application is hereby incorporated by reference in its entirety into the present application.

BACKGROUND

There are several types of medical devices that stimulate nerve, muscle or other tissue fibers in a recipient. For example, hearing prostheses commonly referred to as cochlear implants electrically stimulate auditory neurons to evoke a hearing percept in a recipient.

Cochlear implants typically include a sound input device such as a microphone that receives ambient sound, and a sound processor that converts selected portions of the received sound into encoded control signals which drive an implanted stimulator that generates corresponding stimulation signals. The stimulation signals are delivered to the cochlea via an array of electrode contacts disposed on an elongate electrode assembly implanted within or adjacent to the cochlea.

SUMMARY

Various aspects of the technology described herein are directed toward a cochlear implant electrode assembly insertion tool. In one aspect, an insertion tool having an insertion guide tube is disclosed. The insertion tool is configured to maintain a pre-curved electrode assembly in a substantially straight configuration while preventing the electrode assembly from twisting in response to stresses induced by bias forces which urge the assembly to return to its pre-curved configuration.

BRIEF DESCRIPTION OF THE DRAWINGS

Aspects and embodiments of the subject matter disclosed herein are presented in conjunction with the accompanying drawings, in which.

DETAILED DESCRIPTION

Figure 1:
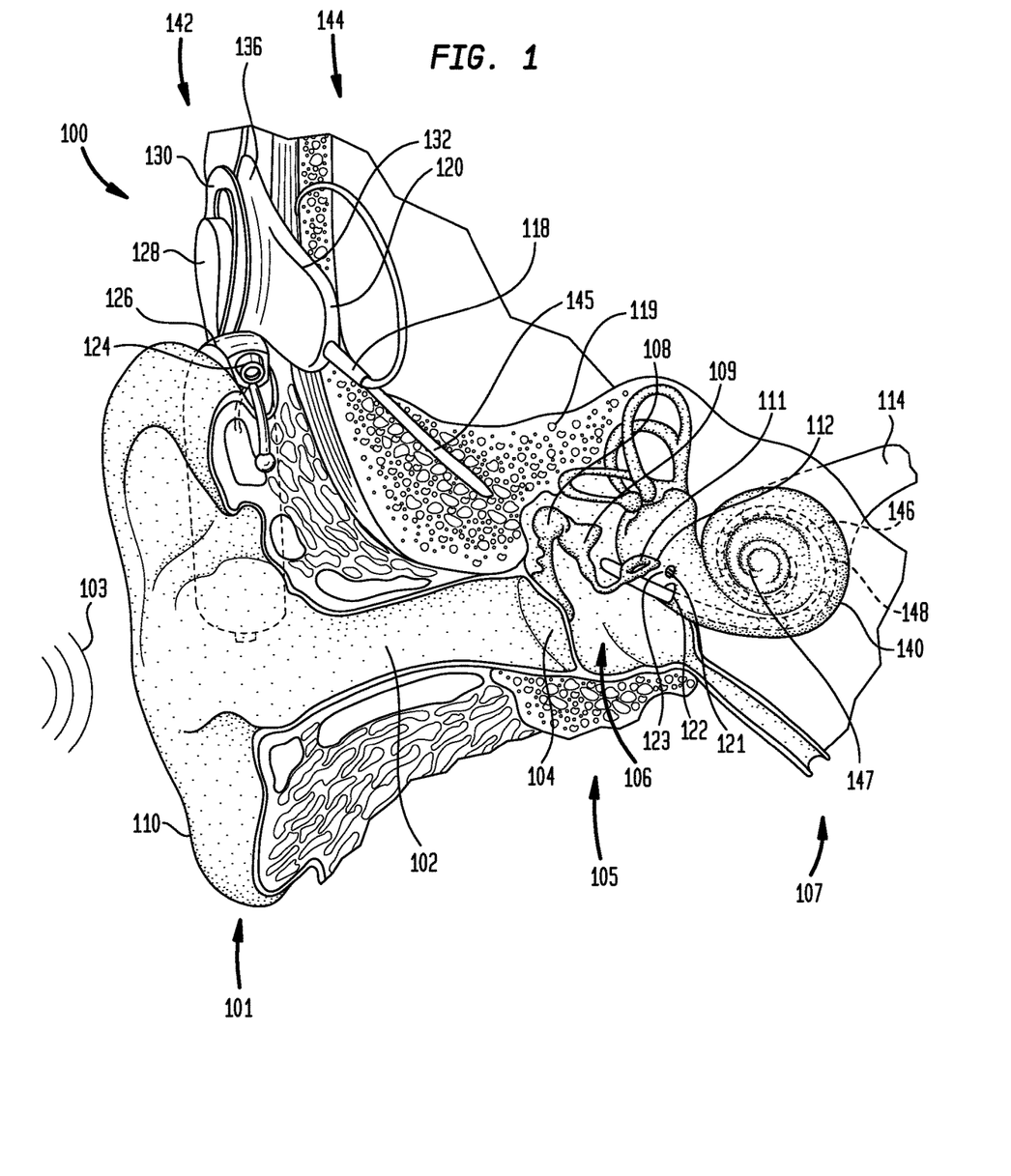
FIG. 1 is a perspective view of an exemplary stimulating medical device, namely a a cochlear implant, which may be advantageously implanted in a recipient using an embodiment of an insertion tool described herein.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear cannel 102 is a tympanic membrane 104 that vibrates in response to sound waves 103. This vibration is coupled to oval window or fenestra ovalis 112 through the three bones of the middle ear 105, collectively referred to as the ossicles 106 and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123 or an opening in an apical turn 147 of cochlea 140. Integrated in electrode assembly 145 is an array 146 of longitudinally-aligned and distally extending electrode contacts 148 for stimulating the cochlea by delivering electrical, optical or other form of energy. Stimulator unit 120 generates stimulation signals each of which is delivered by a specific electrode contact 148 to cochlea 140, thereby stimulating auditory nerve 114.

Figure 2:
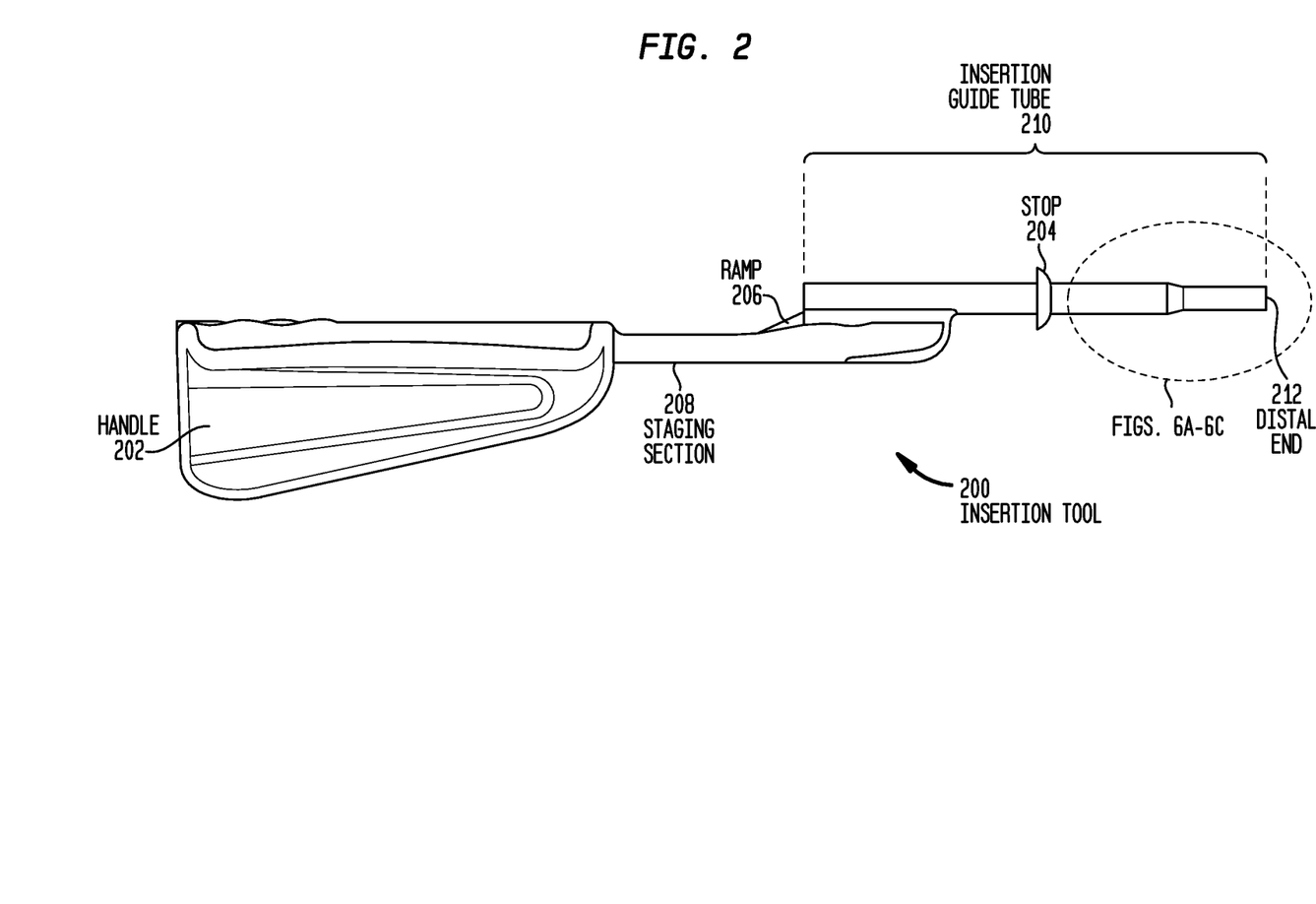
FIG. 2 is a side view of an embodiment of an insertion tool for implanting a cochlear implant electrode assembly such as the electrode assembly illustrated in FIG. 1.

Electrode assembly 145 may be inserted into cochlea 140 with the use of an insertion tool. FIG. 2 is a side view of an embodiment of an insertion tool for implanting an elongate electrode assembly generally represented by electrode assembly 145 into a mammalian cochlea, represented by cochlea 140. The illustrative insertion tool, referred to herein as insertion tool 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A handle 202 is mounted to a proximal end of staging section 208 to facilitate implantation. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 3A:
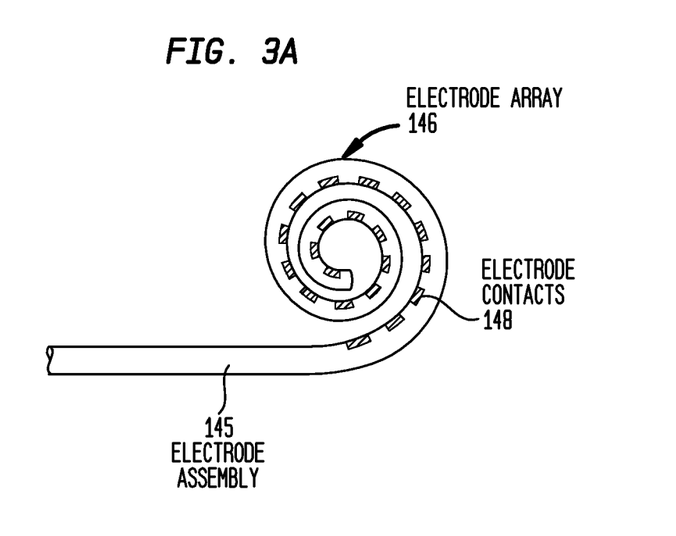
FIGS. 3A and 3B are side and perspective views of an electrode assembly extended out of an embodiment of an insertion sheath of the insertion tool illustrated in FIG. 2.
Figure 3B:
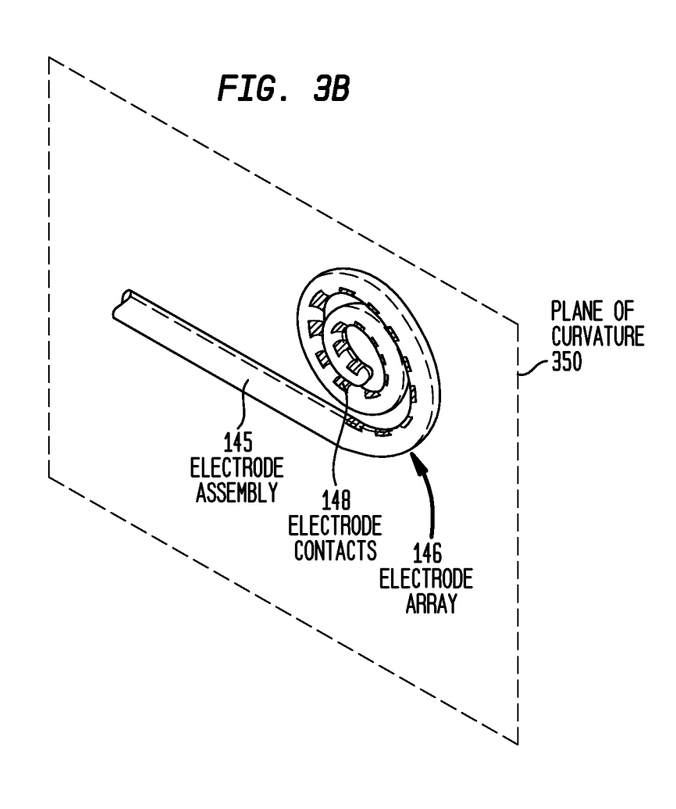

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve so that it is able to conform to the curved interior of cochlea 140. As shown in FIG. 3B, when not in cochlea 140, electrode assembly 145 generally resides in a plane 350 as it returns to its curved configuration.

Figure 4A:
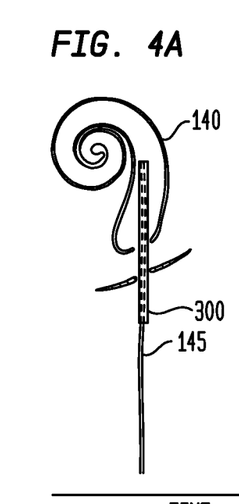
FIGS. 4A-4E are simplified side views depicting the position and orientation of a cochlear implant electrode assembly insertion guide tube relative to the cochlea at each of a series of successive moments during an exemplary implantation of the electrode assembly into the cochlea.

FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly returning to its precurved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is precurved to have a radius of curvature that approximates the curvature of medial side of the scala tympani of the cochlea. Such embodiments of the electrode assembly are referred to as a perimodiolar electrode assembly and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

Figure 4B:
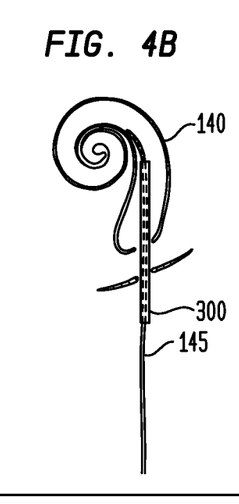
Figure 4C:
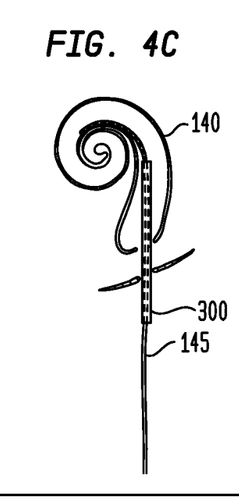
Figure 4D:
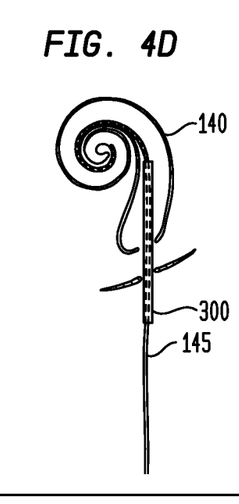
Figure 4E:
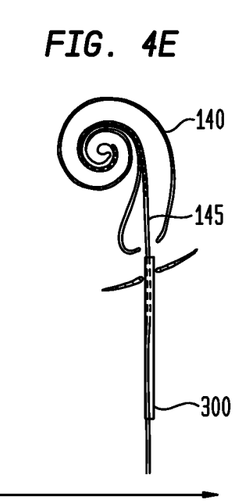

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly as this causes the electrode contacts to face the modiolus when the electrode assembly is implanted in or adjacent to cochlea 140. Insertion guide tube 500 retains electrode assembly 145 in a substantially straight configuration, thereby preventing the assembly from taking on the configuration shown in FIG. 3B. The inability of electrode assembly 145 to curve to accommodate the bias force induces stress in the assembly. Pre-curved electrode assembly 145 will tend to twist while exiting insertion guide tube 510 to reduce this stress. With the distal end of the electrode assembly curved to abut the lumen wall, the assembly twists proximally.

Figure 5A:
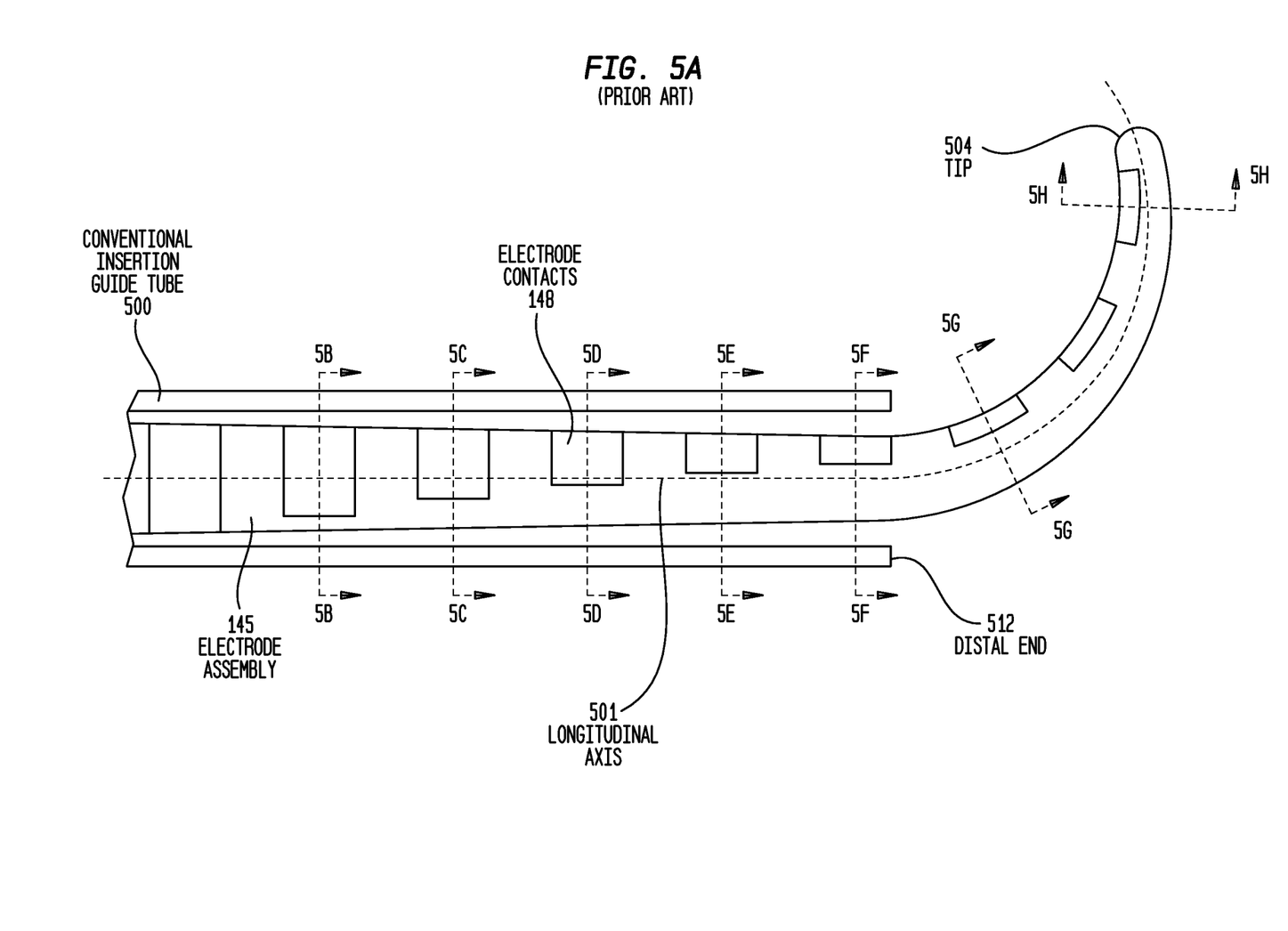
FIG. 5A is a side view of a perimodiolar electrode assembly partially extended out of a conventional insertion guide tube showing how the assembly may twist while in the guide tube.
Figure 5B:
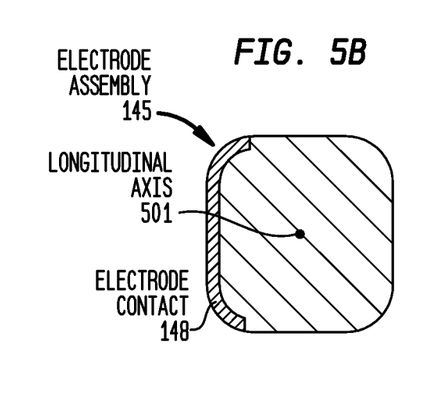
FIGS. 5B-5I are cross-sectional views of the electrode assembly illustrated in FIG. 5A.
Figure 5C:
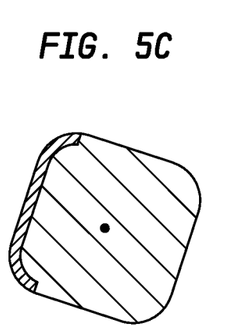
Figure 5D:
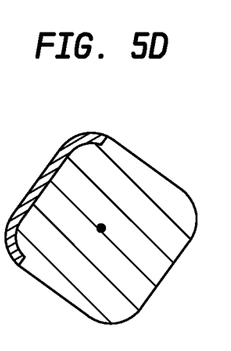
Figure 5E:
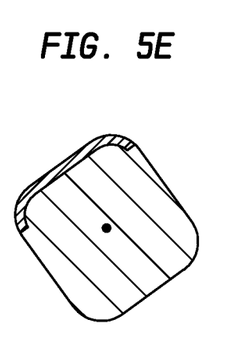
Figure 5F:
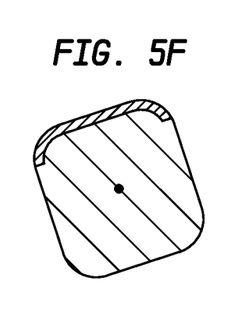
Figure 5G:
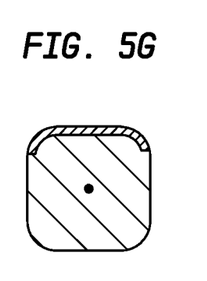
Figure 5H:
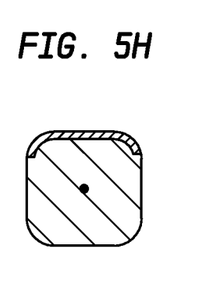
Figure 5I:
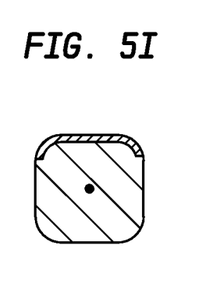

This is illustrated in FIGS. 5A-5I. FIG. 5A is a side view of perimodiolar electrode assembly 145 partially extended out of a conventional insertion guide tube 500 showing how the assembly may twist while in the guide tube. FIGS. 5B-5F are cross-sectional views taken through respective sections 5B-5B, 5C-5C, 5D-5D, 5E-5E, and 5F-5F of electrode assembly 145 in FIG. 5A.

As shown in FIGS. 5A-5F, the portion of electrode assembly 145 in insertion guide tube 510 is twisted about its longitudinal axis resulting in electrode contacts 148 in the twisted region to have a different radial position relative to insertion guide tube 510. As shown in FIGS. 5A and 5G-I, as electrode assembly 145 exists insertion guide tube 500, the assembly is free to curve in accordance with its bias force. However, the orientation of electrode contacts in the deployed region of the assembly is adversely affected by the twisted region of the assembly remaining in guide tube 510.

Accordingly, some embodiments detailed herein and/or variations thereof are directed towards an insertion tool having an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This generally ensures that when the electrode assembly is deployed from the distal end of the insertion guide tube, the electrode assembly and insertion guide tube have a known relative orientation.

Figure 6A:
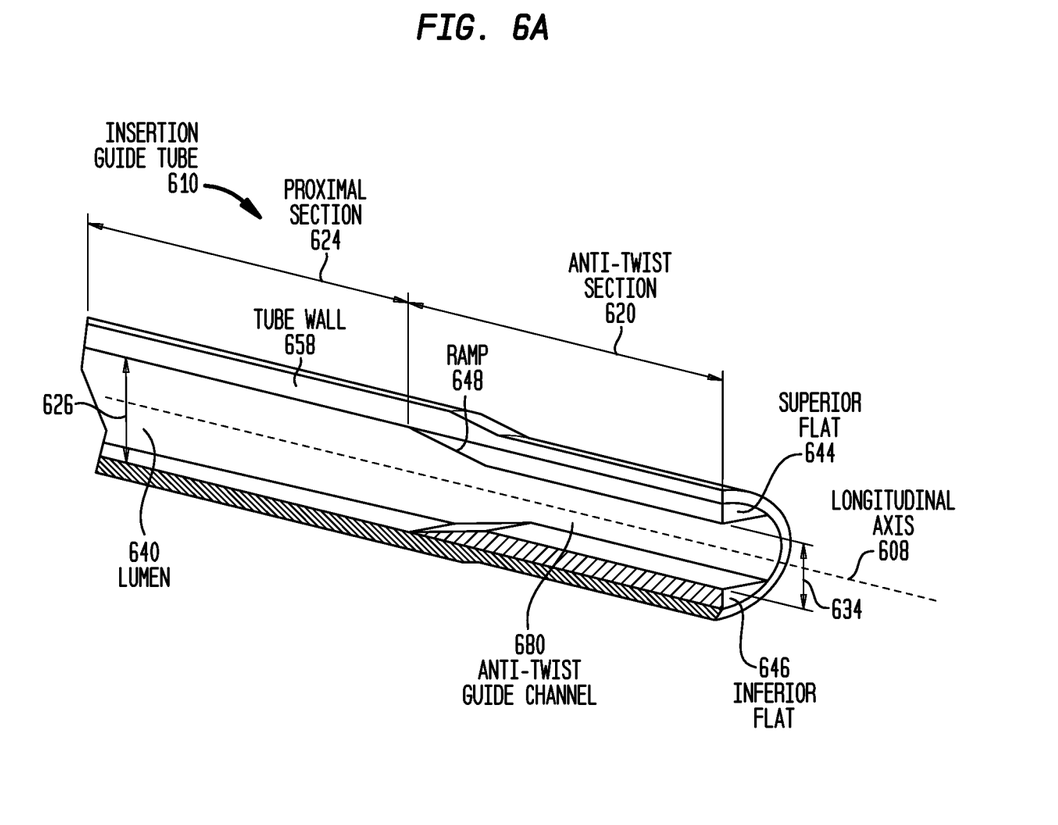
FIG. 6A is a cross-sectional view of an embodiment of the insertion guide tube.
Figure 6B:
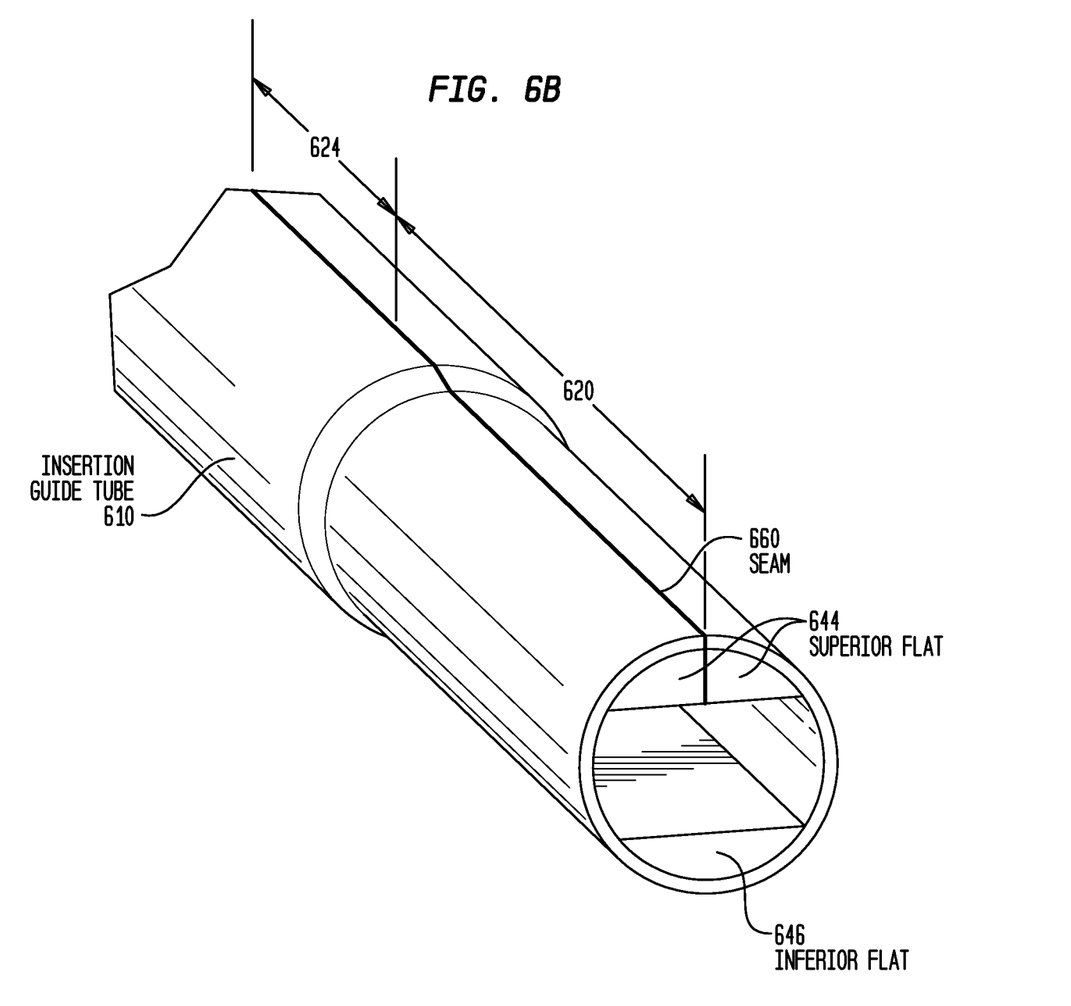
FIG. 6B is a perspective view of the portion of the guide tube illustrated in FIG. 6A.

FIGS. 6A-7B are different views of embodiments of insertion guide tube 210, referred to herein at insertion guide tube 610. For ease of description, features of the guide tube will be described with reference to the orientation of the guide tube illustrated in the figures. FIG. 6A is a partial cross-sectional view of an embodiment of insertion guide tube 210, referred to herein at insertion guide tube 610. As may be seen, insertion guide tube 610 includes an anti-twist section 620 formed at the distal end of the guide tube. Anti-twist section 320 is contiguous with the remaining part of guide tube 610. Guide tube 610 has a lumen 640 which, in proximal section 624 has a vertical dimension 626 and in distal anti-twist section 620 has a smaller vertical dimension 634 described below. The vertical dimension of lumen 640 decreases from dimension 626 to dimension 634 due to a ramp 648 at the proximal end of anti-twist section 642.

Anti-twist section 620 causes a twisted electrode assembly traveling through guide tube 610 to return to its untwisted state, and retains the electrode assembly in a straight configuration such that the orientation of the electrode assembly relative to the insertion guide tube 610 does not change.

Figure 6C:
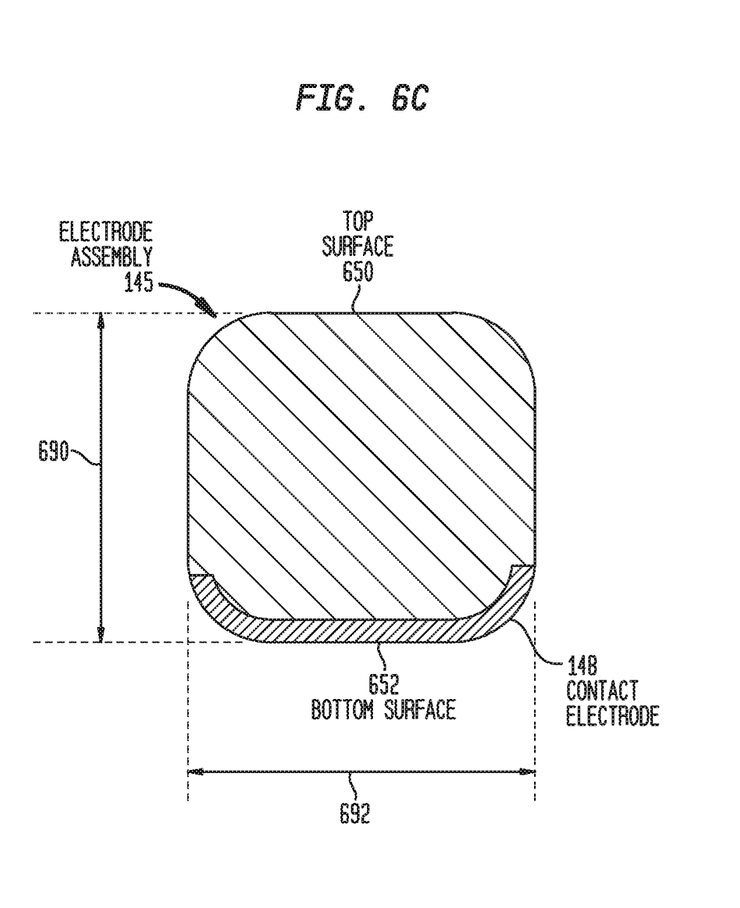
FIG. 6C is a cross-sectional view of a conventional electrode assembly.

As shown in FIG. 6C, electrode assembly 145 has a rectangular cross-sectional shape, with the surface formed in part by the surface of the electrode contact, referred to herein as bottom surface 652, and the opposing surface, referred to herein as top surface 650, are substantially planar. These substantially planar surfaces are utilized in embodiments of the insertion guide described herein.

Figure 6D:
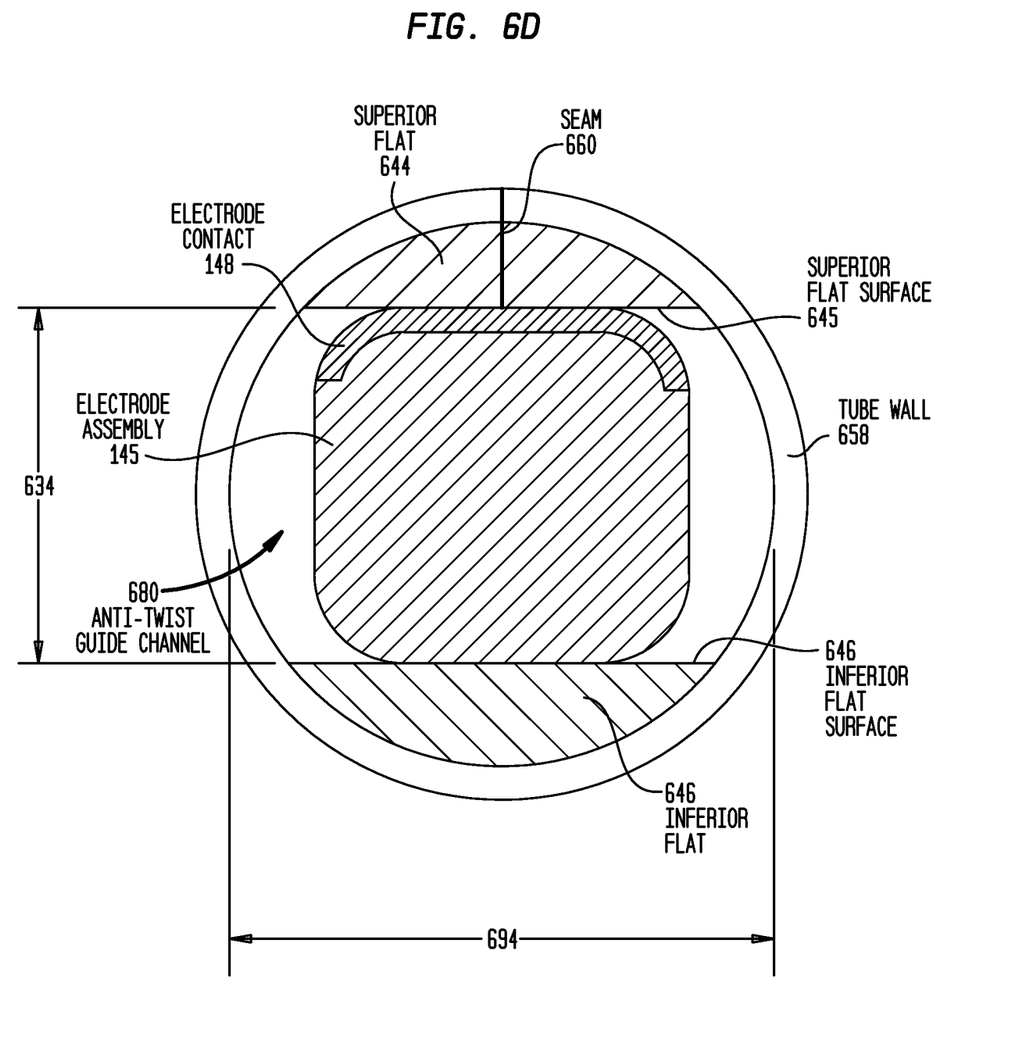
FIG. 6D is a cross-sectional view of the conventional electrode assembly of FIG. 6C positioned in the insertion guide tube illustrated in FIGS. 6A and 6B.

Tube wall 658 in anti-twist section 620 has surfaces 644 and 646 which extend radially inward to form an anti-twist guide channel 680. Specifically, a superior flat 644 provides a substantially planar lumen surface along the length of section 620. As shown best in FIGS. 6A, 6B and 6D, superior flat 644 has a surface that is substantially planar and which therefore conforms with the substantially planar top surface 650 of electrode assembly 145. Similarly, inferior flat 646 has a surface that is substantially planar which conforms with the substantially planar bottom surface 652 of electrode assembly 145. As shown in FIG. 6D, when a distal region of electrode assembly 145 is located in anti-twist section 620, the surfaces of superior flat 644 and inferior flat 646 are in physical contact with top surface 650 and bottom surface 652, respectively, of the electrode assembly. This prevents the electrode assembly from curving, as described above.

Figure 7A:
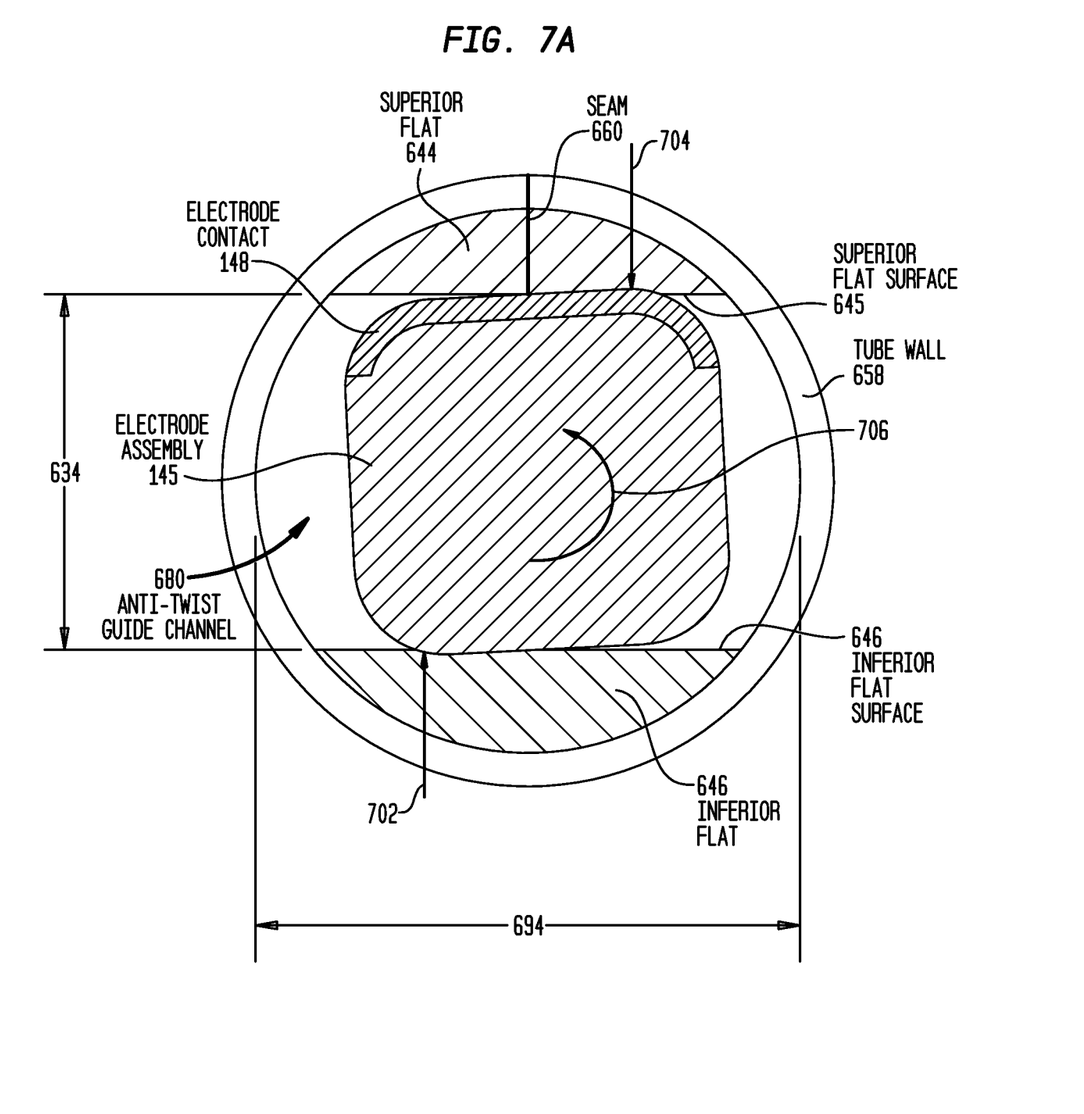
FIG. 7A is the same image shown in FIG. 6D with arrows representing the twisting force of the electrode assembly and the reactive force applied to the electrode assembly by the insertion guide tube.

And, due to the longitudinal length of anti-twist guide channel 680, electrode assembly 145 is unable to twist to relieve the stress caused by the inability of the electrode assembly to assume its pre-curved configuration. This is illustrated in FIG. 7A. As shown by arrow 706, electrode assembly 145 is attempting to twist while located in anti-twist section 620. As top surface 650 of electrode assembly 145 pushes against superior flat 644, the flat applies a reactive force 704 to the assembly. Similarly, as bottom surface 652 of electrode assembly 145 applies a force against inferior flat 646, that flat applies a reactive force 702 to the assembly.

Figure 7B:
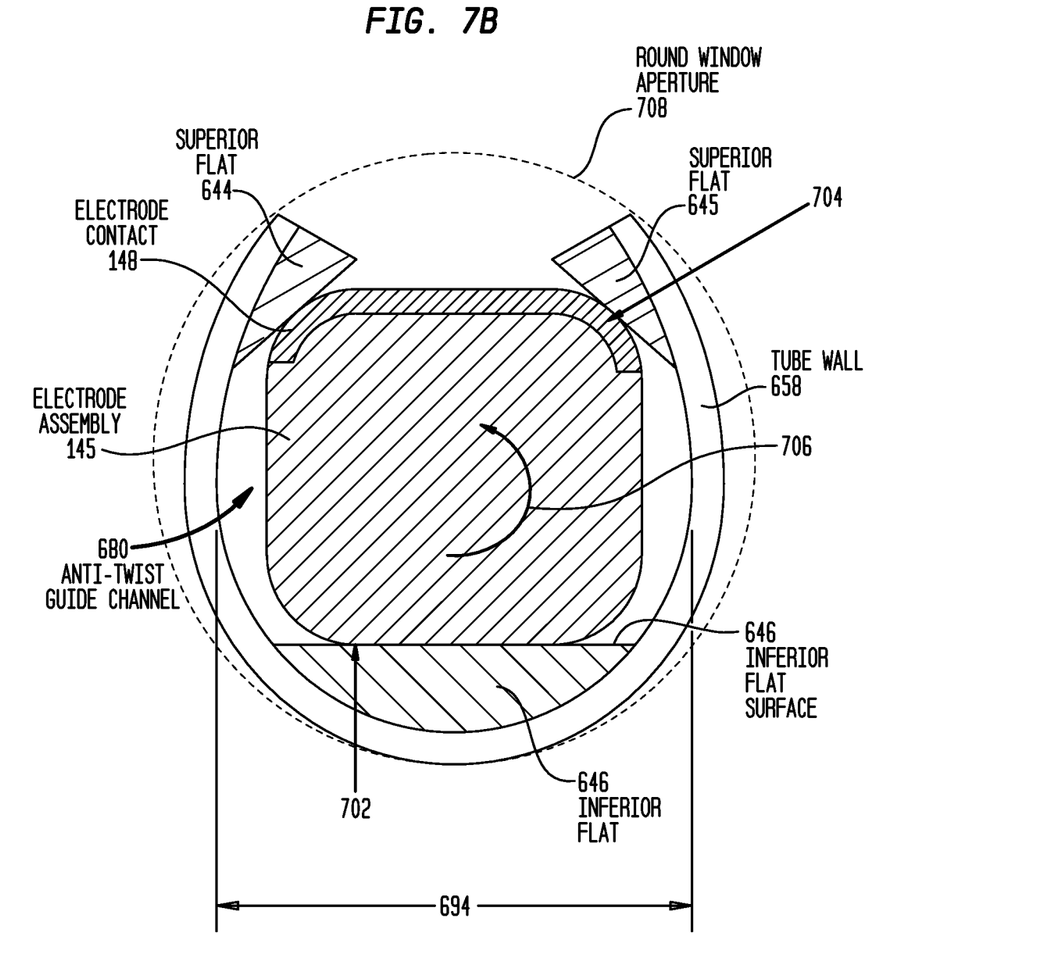
FIG. 7B is the same cross-sectional view illustrated in FIG. 7A with the insertion guide tube splayed open to accommodate a larger-dimensioned proximal region of the electrode assembly, with arrows representing the twisting force of the electrode assembly and the reactive forces applied to the electrode assembly by the insertion guide tube.

As noted, electrode assemblies are longitudinally tapered. to accommodate the increasingly larger cross-sectional dimensions of an electrode assembly 145 as it passes through anti-twist guide channel 680, insertion guide tube 610 has a longitudinal seam 660 as shown in FIGS. 6A, 6B, 6D, 7A and 7B. This seam enables insertion tube 610 to splay open as shown in FIG. 7B. Specifically, insertion tube 610 opens as the vertical distance 690 from bottom surface 652 to top surface 650 of the portion of the assembly in guide channel 680 becomes greater than the vertical distance 634 between the surfaces of inferior flat 646 and superior flat 644.

Once electrode assembly 145 is inserted into cochlea 140, insertion guide tube 610 is retracted over electrode assembly 145. The expanded insertion guide tube 610 is to be withdrawn from cochlea 140 and therefore is to pass through the cochleostomy, oval or round window. In a round window insertion, for example, splayed insertion guide tube 610 is to pass through round window aperture 708.

As electrode assembly 145 is advanced through insertion guide tube 610, the tendency of the assembly to twist decreases. This is due to the increasingly greater portion of the electrode assembly which has been deployed, the relatively larger dimensions of the proximal regions of the assembly, and the relatively smaller bias force in the proximal region as compared to the distal region of the assembly. Thus, as the cross-sectional size of the assembly passing through guide channel 680 increases, the tendency of the electrode assembly to twist decreases. Referring again to FIG. 7B, as insertion guide tube 610 splays, the halves of bifurcated superior flat 348 each translate laterally to the corners of the electrode assembly, and ultimately to opposing sides of the assembly. Thus, the extent to which superior flat 644 prevents the twisting of the electrode assembly decreases with the tendency of the assembly to twist. And as noted, the outside diameter of insertion guide tube 610 does not exceed threshold value(s) which facilitate the withdrawal of the guide tube. In the example noted above with reference to FIGS. 7A and 7B, for example, insertion guide tube 610 has a diameter that is less than the round window aperture 708 when the guide tube is and is not splayed.

As shown in FIG. 6D, lumen 640 has a lateral dimension or width 694 which is greater than the analogous lateral dimension or width 692 of the distal region of electrode assembly 145. This space is dimensioned to receive the wider electrode assembly as the larger proximal region passes through guide channel 680. This is described in greater detail below.

In anti-twist section 620 there is a minimal gap, if any, between flats 644, 646 and electrode assembly 145, thereby enabling anti-twist guide channel 680 to closely control the orientation of the assembly, as noted above. Should a region of electrode assembly 145 located in proximal section 624 be partially twisted relative to a region that is in anti-twist guide channel 680, ramps 648 facilitate the rotation of the assembly as it enters the guide channel. This eliminates the relative twist of this region relative to a more distal region of the assembly. This places top and bottom surfaces 650, 652 in parallel with the corresponding surfaces of superior flat 644 and inferior flat 646 thereby enabling the assembly to continue through anti-twist guide channel 680. In other words, for the assembly to travel through guide channel 680, the assembly has to be substantially straight. As the assembly travels up ramp 648, the ramp facilitates the rotation of the assembly to enable the assembly to enter guide channel 680.

In an exemplary embodiment, insertion guide tube 610 is made of polyimide, and the flats comprise silicone molded in the tube. Other materials can be utilized in other embodiments. In some embodiments, the flats and guide tube are unitary.

As will be understood by those of ordinary skill in the art, the counter-forces 702, 704 are applied such that the forces are offset from the center of the electrode assembly. In this regard, at least in embodiments where the cross-sectional shape of the electrode assembly is not perfectly circular, flats 644, 646 can impart a counter-force to the electrode assembly without substantially relying on friction between the assembly and flats. Such may be the case for electrode assemblies having an elliptical cross-section or the like, etc.

While various embodiments have been described above, it should be understood that they have been presented by way of example only, and not limitation. It will be apparent to persons skilled in the relevant art that various changes in form and detail can be made therein without departing from the scope of the teachings. Thus, the breadth and scope of the teachings herein should not be limited by any of the above-described exemplary embodiments, but should be defined only in accordance with the following claims and their equivalents.

What is claimed is:

1. A method comprising: advancing a pre-curved electrode assembly through a guide tube while controlling an orientation of the electrode assembly relative to the guide tube, thereby deploying the electrode assembly from the guide tube at a predetermined orientation, wherein advancing the pre-curved electrode assembly through the guide tube while controlling the orientation comprises: preventing at least a portion of the electrode assembly from twisting and maintaining a portion of the electrode assembly in a substantially straight configuration.

2. The method of claim 1, wherein advancing the pre-curved electrode assembly through the guide tube while controlling the orientation comprises resisting stresses induced by a bias that urges the electrode assembly to take a pre-curved configuration.

3. The method of claim 1, wherein controlling the orientation comprises maintaining a radial position of electrode contacts of the electrode assembly relative to the guide tube.

4. The method of claim 1, further comprising reducing a twist of a region of the electrode assembly relative to a more distal region of the electrode assembly as the electrode assembly is advanced through the guide tube.

5. The method of claim 4, wherein reducing the twist comprises advancing the electrode assembly along a ramp of the guide tube.

6. The method of claim 1, further comprising:
inserting the guide tube into a cochlea of a recipient; and
deploying the electrode assembly from the guide tube at the predetermined orientation into a perimodiolar position within the cochlea.

7. A method comprising:
advancing a pre-curved electrode assembly though an insertion guide having an open proximal end and an open distal end;
maintaining a portion of the pre-curved electrode assembly in a substantially straight configuration between the open proximal end and the open distal end; and
resisting the electrode assembly from twisting in response to stresses induced by bias forces as the pre-curved electrode assembly exits the open distal end of the insertion guide.

8. The method of claim 7, wherein maintaining the portion of the electrode assembly in the substantially straight configuration comprises facilitating rotation of the electrode assembly to reduce a relative twist.

9. The method of claim 8, further comprising laterally translating at least two parts of the insertion guide by applying force thereto.

10. The method of claim 8, further comprising: inserting a distal end of an insertion guide tube into a cochlea of a recipient; and advancing the electrode assembly through the insertion guide tube.

11. The method of claim 7, further comprising inserting the insertion guide into a cochlea of a recipient.

12. A method of advancing a pre-curved electrode assembly into a cochlea of a recipient, the method comprising:
maintaining the pre-curved electrode assembly in a substantially straight configuration and resisting the electrode assembly twisting in response to stresses induced by bias forces that urge the electrode assembly to return to a pre-curved configuration.

13. The method of claim 12, further comprising: advancing a perimodiolar electrode assembly into the cochlea of the recipient.

14. The method of claim 13, further comprising: causing the perimodiolar electrode assembly to untwist as the electrode assembly is advanced.

15. The method of claim 13, further comprising: applying a force to the pre-curved electrode assembly to resist twisting of the electrode assembly.

16. The method of claim 12, further comprising: causing an insertion guide tube to splay open along a longitudinal seam as the electrode assembly exits the insertion guide tube.

17. The method of claim 12, further comprising: advancing the pre-curved electrode assembly into the cochlea of the recipient; and causing the electrode assembly to adopt a position adjacent a modiolar wall of the cochlea.

18. The method of claim 16, further comprising: advancing the pre-curved electrode assembly from a distal end of the insertion guide tube into the cochlea of the recipient.

* * * * *